(12) United States Patent
Hoffmann et al.

(10) Patent No.: US 6,755,859 B2
(45) Date of Patent: Jun. 29, 2004

(54) IRIS FIXATED INTRAOCULAR LENSES

(75) Inventors: Laurent G. Hoffmann, Foucherans (FR); Donald Carrol Stenger, Anaheim Hills, CA (US)

(73) Assignee: Bausch & Lomb Incorporated, Rochester, NY (US)

( * ) Notice: Subject to any disclaimer, the term of this patent is extended or adjusted under 35 U.S.C. 154(b) by 0 days.

(21) Appl. No.: 10/430,827

(22) Filed: May 6, 2003

(65) Prior Publication Data

US 2003/0195622 A1 Oct. 16, 2003

Related U.S. Application Data

(63) Continuation of application No. 09/734,401, filed on Dec. 11, 2000, now abandoned.

(51) Int. Cl.[7] .................................................. A61F 2/16
(52) U.S. Cl. ..................... 623/6.43; 623/6.45; 623/6.47
(58) Field of Search ............................. 623/6.11, 6.14, 623/6.15, 6.18, 6.38, 6.4, 6.43, 6.45–6.55

(56) References Cited

U.S. PATENT DOCUMENTS

| | | | |
|---|---|---|---|
| 4,014,049 A | 3/1977 | Richards | 3/13 |
| 4,177,526 A | 12/1979 | Kuppinger | 3/13 |
| 4,203,168 A | 5/1980 | Rainin | 3/13 |
| 4,215,440 A | 8/1980 | Worst | 3/13 |
| 4,285,072 A | 8/1981 | Morcher | 3/13 |
| 4,340,979 A | 7/1982 | Kelman | 3/13 |
| 4,361,913 A | 12/1982 | Streck | 3/13 |
| 4,404,694 A | 9/1983 | Kelman | 3/13 |
| 4,435,855 A | 3/1984 | Pannu | 3/13 |
| 4,437,194 A | 3/1984 | Hahs | 3/13 |
| 4,442,553 A | 4/1984 | Hessburg | 3/13 |
| 4,485,499 A | 12/1984 | Castleman | 3/13 |
| 4,504,981 A | 3/1985 | Walman | 3/13 |
| 4,542,540 A | 9/1985 | White | 623/6 |
| 4,542,541 A | 9/1985 | Pannu | 623/6 |
| 4,547,914 A | 10/1985 | Castleman | 623/6 |
| 4,547,915 A | 10/1985 | Castleman | 623/6 |
| 4,629,462 A | 12/1986 | Feaster | 623/6 |
| RE32,525 E | 10/1987 | Pannu | 623/6 |
| 4,702,865 A | 10/1987 | Koziol | 264/17 |
| 4,711,638 A | 12/1987 | Lindstrom | 623/6 |
| 4,787,902 A | 11/1988 | Sheets | 623/6 |
| 5,133,748 A | 7/1992 | Feaster | 623/6 |
| 5,192,319 A | 3/1993 | Worst | 623/6 |
| RE34,424 E | 10/1993 | Walman | 623/6 |
| 5,476,514 A | 12/1995 | Cumming | 623/6 |
| 5,496,366 A | 3/1996 | Cumming | 623/6 |
| 5,571,177 A | 11/1996 | Deacon | 623/6 |
| 5,611,968 A | 3/1997 | Grisoni | 264/2.1 |
| 5,628,796 A | 5/1997 | Suzuki | 623/6 |
| 5,674,282 A | 10/1997 | Cumming | 623/6 |
| 5,697,973 A | 12/1997 | Peyman | 623/6 |
| 5,766,244 A | 6/1998 | Binder | 623/6 |
| 5,776,191 A | 7/1998 | Mazzocco | 623/6 |
| 5,968,094 A | 10/1999 | Weblin | 623/6 |

(List continued on next page.)

FOREIGN PATENT DOCUMENTS

| | | | |
|---|---|---|---|
| EP | 0492126 A2 | 11/1991 | |
| EP | 0962196 A1 | 12/1999 | |

*Primary Examiner*—Bruce Snow
*Assistant Examiner*—Cheryl Miller
(74) *Attorney, Agent, or Firm*—Katherine McGuire

(57) ABSTRACT

A refractive anterior chamber iris fixated intraocular lens including an optic portion having an outer peripheral edge and two or more but preferably two haptic elements. Each haptic element is manufactured to have an inner portion and an outer free end portion for supporting the optic portion in a patient's eye. The inner portion of each haptic element is preferably permanently connected to the outer peripheral edge of the optic portion. Each haptic element also includes a tissue clasp for secure attachment of the intraocular lens to the non-mobile periphery of the iris of an eye.

18 Claims, 4 Drawing Sheets

U.S. PATENT DOCUMENTS

| | | | |
|---|---|---|---|
| 6,152,959 A | 11/2000 | Portney | 623/6.51 |
| 6,193,656 B1 | 2/2001 | Jeffries | 600/398 |
| 6,197,059 B1 | 3/2001 | Cumming | 623/6.39 |
| 6,261,321 B1 | 7/2001 | Kellan | 623/6.51 |
| 6,280,471 B1 | 8/2001 | Peyman | 623/6.17 |
| 6,302,911 B1 | 10/2001 | Hanna | 623/6.39 |
| 6,395,028 B1 | 5/2002 | Tran | 623/6.44 |
| 6,409,762 B1 | 6/2002 | Pynson | 623/6.39 |
| 6,409,763 B1 | 6/2002 | Brady | 623/6.43 |
| 6,451,056 B1 | 9/2002 | Cumming | 623/6.18 |

IRIS FIXATED INTRAOCULAR LENSES

REFERENCE TO RELATED APPLICATIONS

This application is a continuation of application Ser. No. 09/734,401, filed Dec. 11, 2000, now abandoned.

FIELD OF THE INVENTION

The present invention relates to intraocular lenses (IOLs) and a method for making and using the same. More particularly, the present invention relates to anterior chamber iris fixated IOLs designed primarily for refractive correction in phakic eyes where the eye's natural lens remains intact.

BACKGROUND OF THE INVENTION

Visual acuity deficiencies such as myopia (nearsightedness), hyperopia (farsightedness), presbyopia (age-related farsightedness), aphakia (absence of the crystalline lens of the eye) and astigmatism (irregular conformation of the cornea of the eye) are typically corrected through the use of refractive lenses such as spectacles or contact lenses. Although these types of lenses are effective in correcting a wearer's eyesight, many wearers consider the lenses inconvenient. The lenses must be located, worn at certain times, removed periodically and may be lost or misplaced. The lenses may also be dangerous or cumbersome if the wearer participates in athletic activities or suffers an impact in an area near the eyes.

The use of surgically implanted anterior chamber IOLs as a permanent form of refractive correction has been gaining in popularity. IOL implants have been used for years in the anterior or posterior chamber of aphakic eyes as replacements for surgically removed natural crystalline lenses, which is common in the case of cataracts. Many different IOL designs have been developed over past years and proven successful for use in aphakic eyes. The successful IOL designs to date primarily include an optic portion with supports therefor, called haptics, connected to and surrounding at least a part of the optic portion. The haptic elements of an IOL are designed to support the optic portion of the IOL in the lens capsule, anterior chamber or posterior chamber of an eye once implanted.

Commercially successful IOLs have been made from a variety of biocompatible materials, ranging from more rigid materials such as polymethylmethacrylate (PMMA) to softer, more flexible materials capable of being folded or compressed such as silicones, certain acrylics, and hydrogels. Haptic portions of the IOLs have been formed separately from the optic portion and later connected thereto through processes such as heat, physical staking and/or chemical bonding. Haptics have also been formed as an integral part of the optic portion in what is commonly referred to as "single-piece" IOLs.

Softer, more flexible IOLs have gained in popularity in recent years due to their ability to be compressed, folded, rolled or otherwise deformed. Such softer IOLs may be deformed prior to insertion thereof through an incision in the cornea of an eye. Following insertion of the IOL in an eye, the IOL returns to its original pre-deformed shape due to the memory characteristics of the soft material. Softer, more flexible IOLs as just described may be implanted into an eye through an incision that is much smaller, i.e., 2.8 to 3.2 mm, than that necessary for more rigid IOLs, i.e., 4.8 to 6.0 mm. A larger incision is necessary for more rigid IOLs because the lens must be inserted through an incision in the cornea slightly larger than that of the diameter of the inflexible IOL optic portion. Accordingly, more rigid IOLs have become less popular in the market since larger incisions have been found to be associated with an increased incidence of postoperative complications, such as induced astigmatism.

After IOL implantation, both softer and more rigid IOLs positioned within the angle of the anterior chamber of the eye are subject to compressive forces exerted on the outer edges thereof, which typically occur when an individual squints or rubs the eye. Such compressive forces on angle positioned IOLs in either aphakic or phakic eyes may result in tissue damage, decentration of the IOL and/or distortion of the visual image. Compressive forces exerted on an angle positioned IOL may also tend to cause movement of the IOL haptics and axial displacement of the IOL along the optical axis of an eye. Haptic movement and broad haptic contact in the angle of the anterior chamber of an eye has the potential to cause damage to delicate structures within the eye such as the peripheral corneal endothelium, the trabecular meshwork and/or the iris. Movement of an IOL along the optical axis of an eye has the potential to cause the IOL to contact and damage the delicate corneal endothelial cell layer of the eye. Also, angle positioned IOLs of current designs, whether formed of either softer or more rigid materials, tend to deflect along the optical axis of an eye when the haptics are compressed. IOL manufacturers provide a wide range of IOL sizes to more precisely fit IOLs to each particular patient's eye size. Providing a wide range of IOL sizes is an attempt to minimize the potential for haptic compression and the associated axial displacement of the IOL optic along the optical axis of an eye.

Because of the noted shortcomings of current IOL designs, there is a need for aphakic and phakic anterior chamber IOLs designed to eliminate haptic contact and movement in the angle of the anterior chamber and eliminate axial displacement of the IOL optic portion along the optical axis of the eye when compressive forces are exerted against the outer edges thereof. By eliminating an IOL's haptic and optic movement within the angle and within the anterior chamber, more certain refractive correction may be achieved and the risk of delicate tissue damage may be reduced.

SUMMARY OF THE INVENTION

An anterior chamber iris fixated intraocular lens (IOL) made in accordance with the present invention has an optic portion with an outer peripheral edge and two or more but preferably two haptic elements for supporting the optic portion in a patient's eye. Two haptic elements are preferred in the present invention to provide IOL stability and to minimized points of fixation on the iris. A lens having two haptic elements is balanced or stabilized by having one haptic element formed on one edge of the optic portion and the second haptic element formed on an opposite edge of the optic portion. Both of the haptic elements on the optic portion are preferably of a plate-like form designed to allow the IOL to be easily folded, rolled and/or compressed for implantation thereof within an eye through a relatively small incision preferably using an inserter. Each haptic element is manufactured with an attachment aperture preferably centered in an outer free end portion thereof, an attachment slot formed in conjunction with the attachment aperture and a tissue clasp formed in conjunction with the attachment aperture for ease in securely attaching the tissue clasp on the anterior surface of the iris of an eye. The tissue clasps are designed to secure the IOL within the anterior chamber of an eye by securely engaging the relatively non-mobile outer peripheral edge of the iris of an eye. Each haptic element also has an inner portion opposite the outer free end portion. The inner portion of the haptic element is preferably connected to or integrally formed with the outer peripheral edge of the optic portion of the IOL.

Accordingly, it is an object of the present invention to provide intraocular lenses for use in aphakic and phakic eyes.

Another object of the present invention is to provide intraocular lenses for use in aphakic and phakic eyes, which eliminate anterior chamber angle contact.

Another object of the present invention is to provide intraocular lenses for use in aphakic and phakic eyes, which minimize axial displacement of the optic portions of the lenses along the optical axis of the eyes.

Another object of the present invention is to provide intraocular lenses that allow for increased ease of implantation thereof.

Another object of the present invention is to provide intraocular lenses that allow for implantation using an inserter.

Another object of the present invention is to provide intraocular lenses for use in aphakic and phakic eyes, which minimize damage to tissues in the interior of the eyes.

Still another object of the present invention is to provide intraocular lenses, which are resistant to decentration within the eyes.

These and other objectives and advantages of the present invention, some of which are specifically described and others that are not, will become apparent from the detailed description, drawings and claims that follow, wherein like features are designated by like numerals.

DETAILED DESCRIPTION OF THE INVENTION

Figure 1:
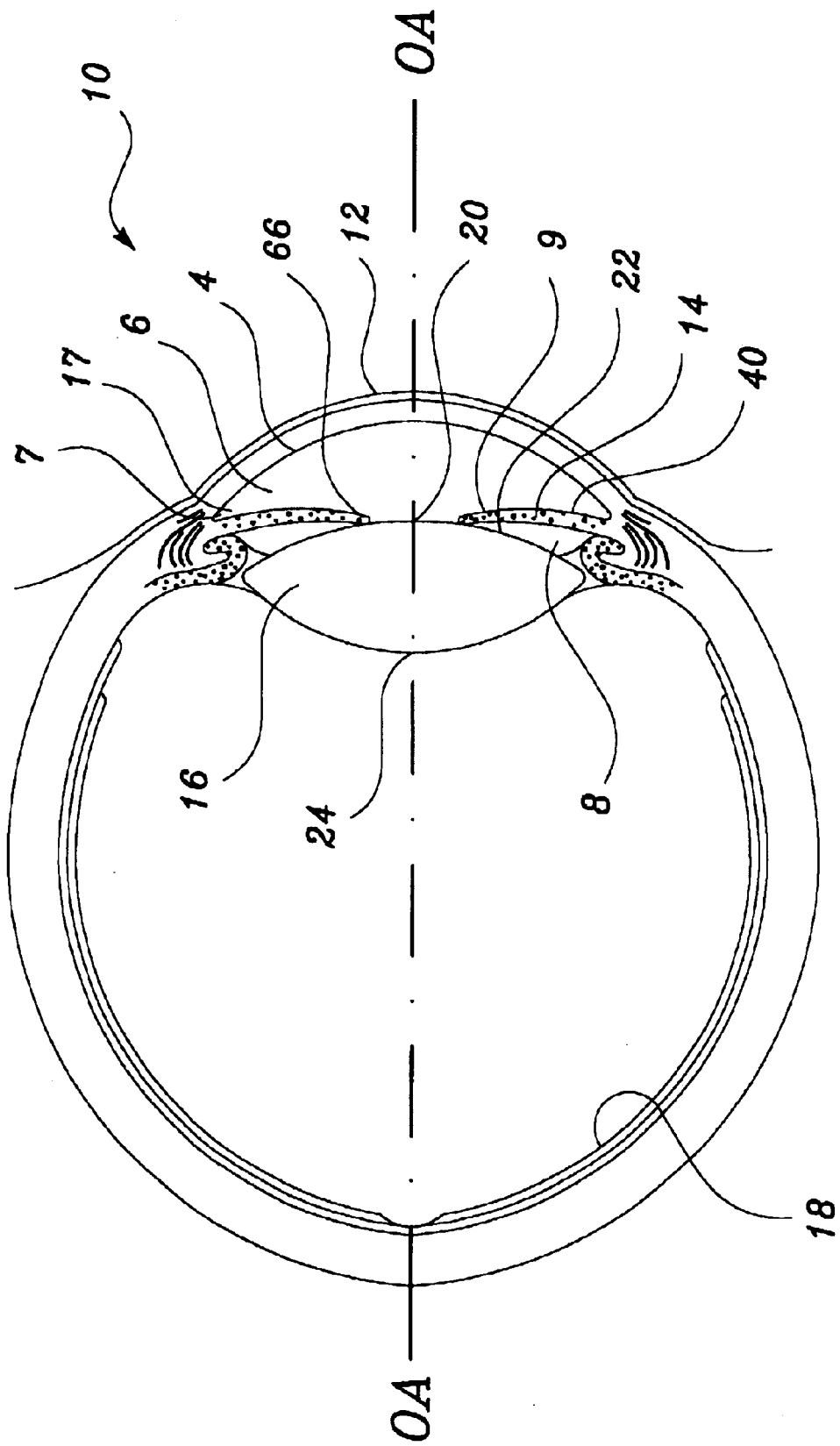
FIG. 1 is a schematic representation of the interior of a phakic human eye including a natural lens and a refractive IOL implanted in the anterior chamber of the eye.

FIG. 1 illustrates a simplified diagram of an eye 10 showing landmark structures relevant to the implantation of an intraocular lens of the present invention. Eye 10 includes an optically clear cornea 12 and an iris 14 with a relatively non-mobile peripheral edge 40. A natural crystalline lens 16 and a retina 18 are located behind iris 14 of eye 10. Eye 10 also includes anterior chamber 6 with angle 7 located in front of iris 14 and a posterior chamber 8 located between iris 14 and natural lens 16. An IOL 26, such as that of the present invention, is preferably implanted in anterior chamber 6 to correct refractive errors while healthy natural lens 16 remains in place (phakic application). However, IOL 26 likewise may be implanted in anterior chamber 6 of aphakic eyes where the natural lens 16 has been removed. Eye 10 also includes an optical axis OA—OA that is an imaginary line that passes through the optical center 20 of anterior surface 22 and posterior surface 24 of lens 16. Optical axis OA—OA in the human eye 10 is generally perpendicular to a portion of cornea 12, natural lens 16 and retina 18.

Figure 2:
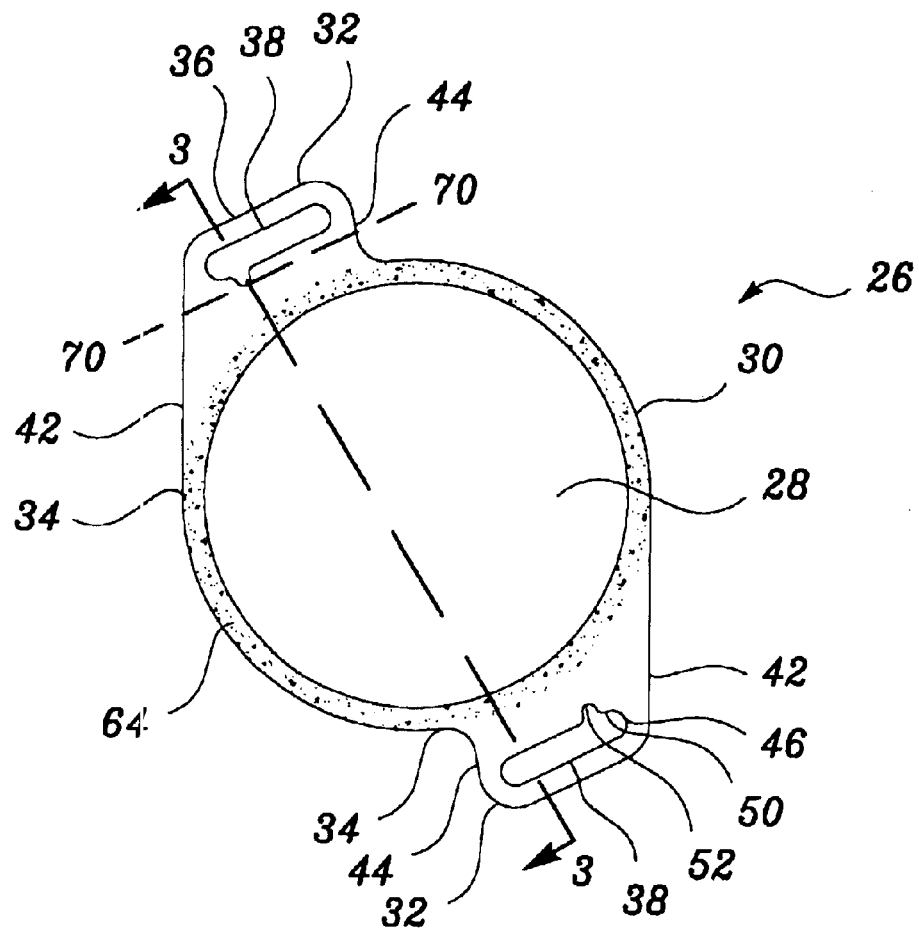
FIG. 2 is a plan view of an IOL with two haptics made in accordance with the present invention.
Figure 4:
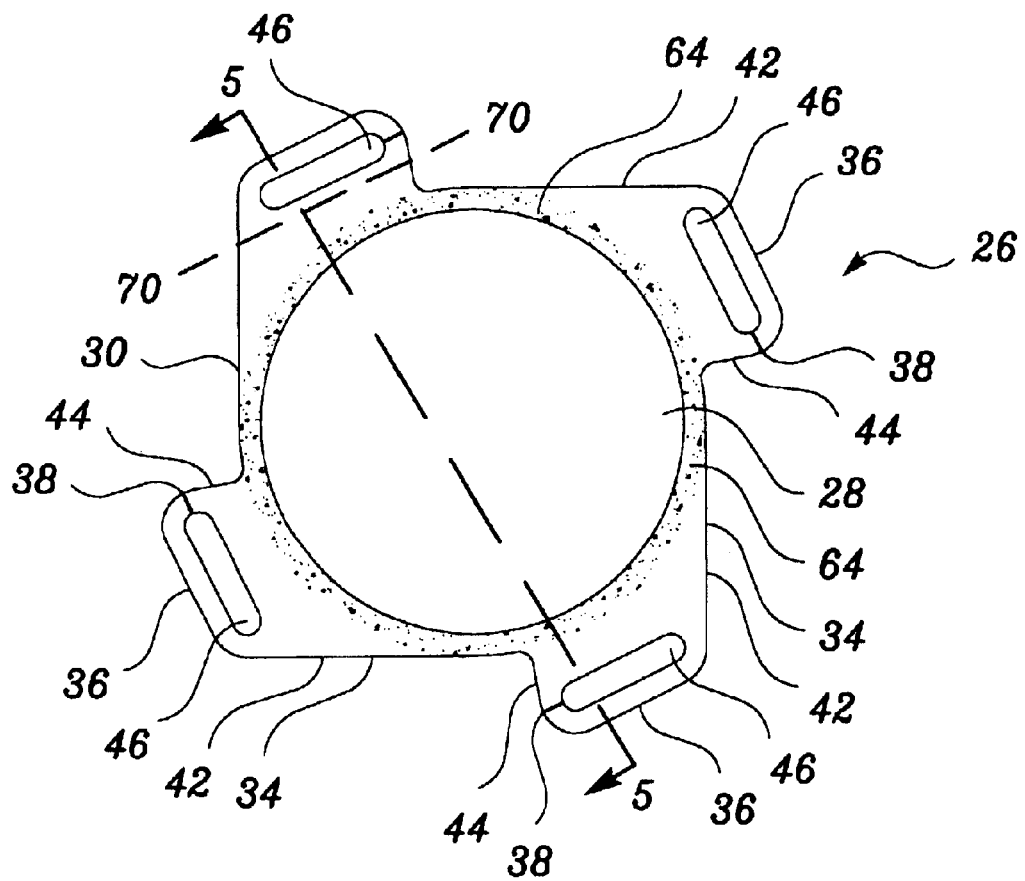
FIG. 4 is a plan view of an IOL with four haptics made in accordance with the present invention.

The IOL of the present invention, as best illustrated in FIGS. 2 and 4 identified by reference numeral 26, is designed for implantation in anterior chamber 6 of a patient's aphakic or phakic eye 10. IOL 26 has an optic portion 28 with an outer peripheral edge 30. Preferably integrally formed on peripheral edge 30 of optic portion 28 are two or more but preferably two separate plate-like haptic elements 32. Each haptic element 32 is manufactured to have an inner portion 34 and an outer free end portion 36. Inner portions 34 of haptic elements 32 are preferably integrally formed with and permanently connected to outer peripheral edge 30 of optic portion 28. Alternatively however, inner portions 34 of haptic elements 32 may be attached to optic portion 28 by staking, chemical polymerization or other methods known to those skilled in the art. Each haptic element 32 also includes at outer free end portion 36, a tissue clasp 38 designed to engage relatively non-mobile outer peripheral edge 40 of iris 14 in anterior chamber 6. In accordance with the present invention, IOL 26 is securely held in proper position in anterior chamber 6 through constant compressive forces exerted by tissue clasp 38 on relatively non-mobile outer peripheral edge 40 of iris 14. Iris fixation of IOL 26 is desired to avoid haptic element 32 contact and damage to delicate tissues within angle 7 of eye 10.

Figure 5:
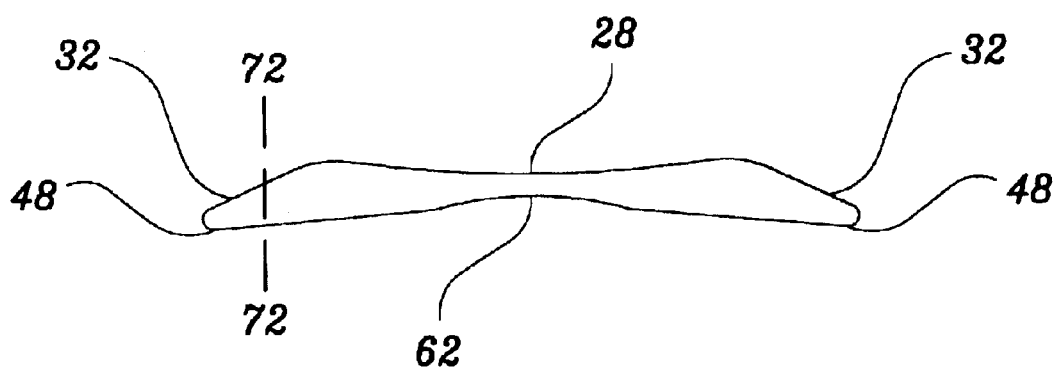
FIG. 5 is a side cross-sectional view of the IOL of FIG. 4 taken along line 5—5.
Figure 6:
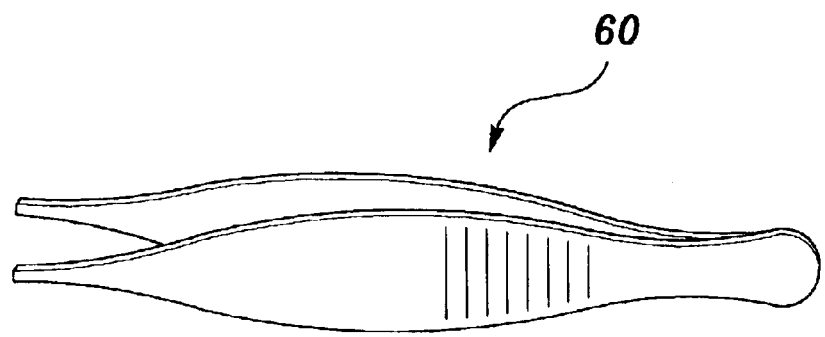
FIG. 6 is a perspective view of a surgical forceps.
Figure 7:
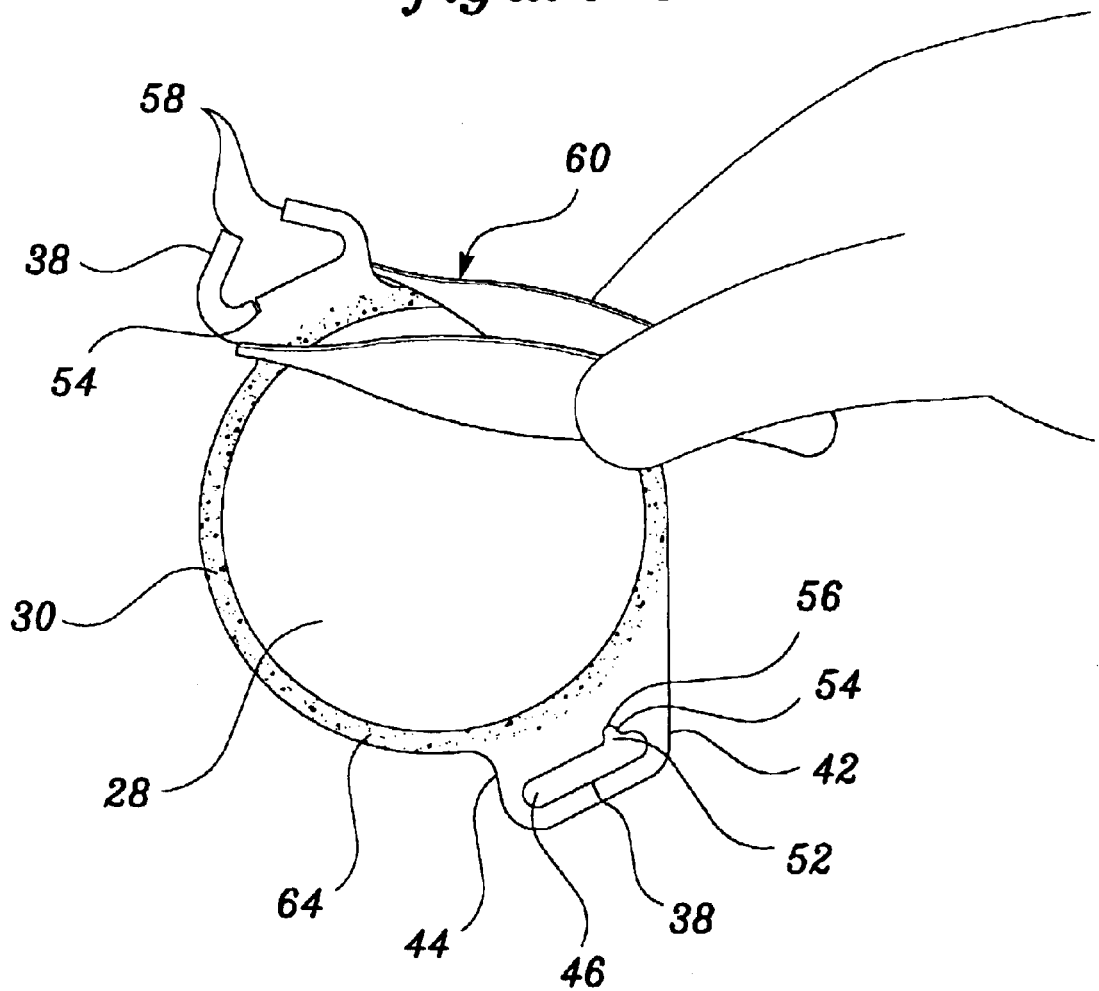
FIG. 7 is a perspective view of the IOL of FIG. 2 with the surgical forceps of FIG. 6 used to open a tissue clasp.

The required functional characteristics of haptic elements 32 to enable single-handed implantation and to maintain adequate compressive forces on iris 14, are achieved through the unique design thereof. Haptic elements 32, as best illustrated in FIGS. 2 through 5, are formed with an inner portion 34, an outer free end portion 36, a tangential haptic edge 42 that is formed tangent to outer peripheral edge 30 of optic portion 28 and an opposed parallel haptic edge 44 that is formed to be parallel with tangential haptic edge 42. The width of outer free end portion 36 if measured in plane 70—70 is preferably between 15 to 40 percent of the diameter of optic portion 28, but preferably approximately 1.5 mm. Haptic elements 32 are offset to be tangent to outer peripheral edge 30 and significantly smaller than the diameter of optic portion 28 to allow IOL 26 to pass relatively easily through an injector nozzle while avoiding folding of haptic elements 32 at tissue clasps 38 formed therein. In using an injector to implant IOL 26, offset haptic elements 32 allow space for an injector plunger to avoid haptic elements 32 and contact outer peripheral edge 30 of optic portion 28 during the injector insertion process. Injector plunger contact and force on peripheral edge 30 of optic portion 28 adjacent to parallel haptic edge 44 is desirable to avoid and prevent damage to haptic element 32 during implantation. Alternatively, IOL 26 may be folded and implanted into an eye using forceps 60 by folding IOL 26 optic portion 28 along an axis adjacent to parallel haptic edges 44 to avoid folding or manipulation of haptic elements 32 to prevent damage thereto. Formed in outer free end portion 36 of haptic element 32, preferably an equal distance between tangential haptic edge 42 and parallel haptic edge 44, is an attachment aperture 46 defined by aperture edge 50. An optional but preferred channel void 52 is likewise formed in haptic element 32 to extend a defined distance of approximately 0.25 to 2.0 mm but preferably approximately 1.0 mm from aperture edge 50 toward optic portion 28. Extending through haptic elements 32 from free haptic edge 48 of outer free end portion 36 through aperture edge 50 is tissue clasp 38. Tissue clasp 38 may be separated or spread apart in plane 70—70 by compressing inner portion 34 of haptic elements 32 with surgical forceps 60 as illustrated in FIGS. 6 and 7. Upon compression of inner portion 34 of haptic elements 32, interior surfaces 54 of channel void 52 are forced into direct contact thus eliminating the approximately 1.0 mm void 56 defined by channel void 52. In eliminating void 56, fissure edges 58 of tissue clasp 38 are correspondingly spread apart or separated. Alternatively, fissure edges 58 of tissue clasp 38 may be opened or separated by applying a force in plane 70—70 to free haptic edge 48 or aperture edge 50, or by applying a shearing force in plane 72—72 to tissue clasp 38, using surgical forceps 60. Once smooth, serrated or toothed fissure edges 58 of tissue clasps 38 are separated or opened, the same may be placed on or in contact with the relatively non-mobile peripheral edge 40 of iris 14 and allowed to return to their original closed position to impart a suitable attachment or fixation force of approximately 5 to 250 millinewtons on iris 14. The fixation force of IOL 26 will vary depending on the characteristic degree of rigidity/flexibility of the material or materials forming haptic elements 32. The more rigid the material, the greater the fixation force. The more flexible the material, the weaker the fixation force. Fissure edges 58 of tissue clasps 38 may close completely, although not preferred, to pierce relatively non-mobile peripheral edge 40 of iris 14 or close partially to a distance of approximately 0.100 mm between fissure edges 58 to pinch relatively non-mobile peripheral edge 40 of iris 14 for reliable secure attachment thereto. Preferably fissure edges 58 of fixation clamps 38 are oriented in a plane perpendicular to the optical axis OA—OA of eye 10 when secured to iris 14 for better tolerance by iris 14 and easier surgical handling during the implantation process. Because haptic elements 32 are relatively small in size, IOL 26 may be implanted in an eye 10 through a relatively small incision, such as less than 4.0 mm, using an inserter.

Figure 3:
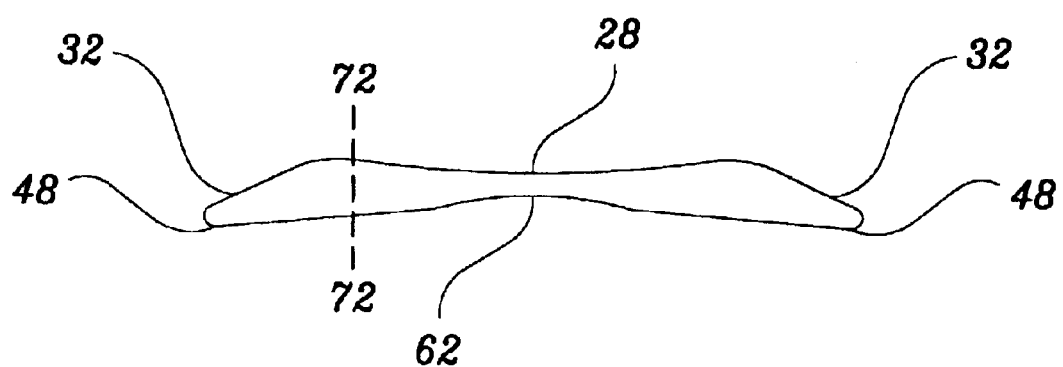
FIG. 3 is a side cross-sectional view of the IOL of FIG. 2 taken along line 3—3.

The subject IOL 26 is preferably produced having an optic portion 28 approximately 4.5 to 9.0 mm, but preferably approximately 5.0 to 6.0 mm and most preferably 5.5 mm in diameter and approximately 0.5 mm to 1.0 mm, but preferably approximately 0.6 to 0.8 mm and most preferably 0.7 mm in thickness at peripheral edge 30. Haptic elements 32 extend in a substantially plate-like configuration and will increase or decrease in length depending upon the diameter of optic portion 28. As the diameter of optic portion 28 increases, the length of haptic elements 32 decrease. Likewise, as the diameter of optic portion 28 decreases, the length of haptic elements 32 increase. In general, haptic elements 32 are formed to be approximately 0.5 to 3.0 mm, but preferably approximately 1.0 to 2.0 mm and most preferably approximately 1.5 mm in length measuring parallel to tangential haptic edge 42 from the center of inner portion 34 to free haptic edge 48. The overall diameter of IOL 26 is approximately 6.0 to 10.0 mm, but preferably approximately 7.0 to 9.0 mm, and most preferably approximately 8.5 mm. Haptic elements 32 are preferably vaulted as illustrated in FIGS. 3 and 5 so optic portion 28 lies in a different but parallel plane to that of free haptic edge 48 of haptic elements 32. Such vaulting of IOL 26 allows appropriate fixation thereof to relatively non-mobile peripheral edge 40 of iris 14 while avoiding contact between the posterior surface 62 of optic portion 28 and mobile portions 9 of iris 14. A vault of approximately 0.5 to 1.0 mm, but preferably 0.75 mm measuring between posterior surface 62 of optic portion 28 and free haptic edge 48 of haptic elements 32 is preferred for central placement of IOL 26 between iris 14 and corneal endothelium 4. Haptic elements 32 vary in thickness in plane 72—72 along the length thereof. Haptic elements 32 are approximately 0.100 to 0.300 mm, but preferably approximately 0.150 mm in thickness at free haptic edge 48 and approximately 0.150 to 1.000 mm, but preferably approximately 0.725 mm in thickness at outer peripheral edge 30. Haptic elements 32 at tissue clasp 38 is approximately 0.100 to 0.400 mm in width in plane 70—70 measuring from free haptic edge 48 to aperture edge 50, but preferably approximately 0.200 mm in width.

Suitable materials for the production of the subject IOL 26 include but are not limited to foldable or compressible materials, such as but not limited to silicone polymers, hydrocarbon and fluorocarbon polymers, hydrogels, soft acrylic polymers, polyesters, polyamides, polyurethane, silicone polymers with hydrophilic monomer units, fluorine-containing polysiloxane elastomers and combinations thereof. It is preferred that IOL 26 is manufactured from a bicomposite material as described in U.S. Pat. Nos. 5,217,491 and 5,326,506 incorporated herein in their entirety by reference. In such a case, optic portion 28 and at least a portion of haptic elements 32 such as inner portions 34 are manufactured from a foldable or compressible material such as but not limited to silicone polymers, hydrocarbon and fluorocarbon polymers, hydrogels, soft acrylic polymers, polyesters, polyamides, polyurethane, silicone polymers with hydrophilic monomer units, fluorine-containing polysiloxane elastomers or combinations thereof. Selecting a compressible, foldable material having a high refractive index is a desirable feature in the production of IOLs to impart high optical power with a minimum of optic thickness. By using a material with a high refractive index, visual acuity deficiencies may be corrected using a thinner IOL. A thin IOL, such as that of IOL 26, is particularly desirable in phakic applications to minimize potentially harmful contact between the IOL 26 and the iris 14 and/or the corneal endothelium 4. Poly(HEMA-co-HOHEXMA) is also a desirable material in the production of IOLs 26 due to its relatively high refractive index and mechanical strength, which is suitable to withstand considerable physical manipulation. Poly(HEMA-co-HOHEXMA) also has desirable memory properties suitable for IOL 26 use. IOLs 26 manufactured from a material possessing good memory properties such as those of poly(HEMA-co-HOHEXMA) unfold in a controlled manner in an eye 10, rather than explosively, to its predetermined shape. Explosive unfolding of IOLs 26 is undesirable due to potential damage to delicate tissues within the eye 10. The remaining portion of haptic elements 32 but most importantly outer free end portion 36 and tissue clasps 38 are preferably manufactured from a relatively more rigid material such as but not limited to a relatively more rigid hydrogel, PMMA or a polyimide. Outer free end portion 36 and tissue clasps 38 are preferably manufactured from a more rigid material to ensure secure attachment to non-mobile peripheral edge 40 of iris 14.

Although the teachings of the present invention are preferably applied to soft or foldable IOLs 26 formed of a foldable or compressible material, the same may also be applied to harder, less flexible lenses formed of one or more relatively rigid materials such as but not limited to polymethylmethacrylate (PMMA) if implantation thereof through a relatively small incision or through an inserter such as that described in U.S. Pat. Nos. 5,873,879, 5,860,986 and 5,810,834, incorporated herein in their entirety by reference, is not desired.

Optic portion 28 of IOL 26 can be a positive powered lens from 0 to approximately +40 diopters or a negative powered lens from 0 to approximately −30 diopters. Optic portion 28 may be biconvex, plano-convex, plano-concave, biconcave or concave-convex (meniscus), depending upon the power required to achieve the appropriate central and peripheral thickness for efficient handling.

Optic portion 28 of the subject IOL 26 may optionally be formed with a glare reduction zone 64 of approximately 0.25 to 0.75 mm but more preferably approximately 0.3 to 0.6 mm and most preferably 0.5 mm in width adjacent outer peripheral edge 30 for reducing glare when outer peripheral edge 30 of IOL 26 is struck by light entering eye 10 during high light or at other times when pupil 66 is dilated. Glare reduction zone 64 is typically fabricated of the same material as optic portion 28, but may be opaque, roughened, textured, colored or patterned in a conventional manner to block or diffuse light in plane with optical axis OA—OA.

The subject IOL 26 may be molded using removable molds as known to those skilled in the art. Alternatively, IOL 26 may be manufactured by first producing discs from one or more materials of choice as described in U.S. Pat. Nos. 5,217,491 and 5,326,506 each incorporated herein in its entirety by reference. IOL 26 may then be machined from the material discs in a conventional manner. Once machined, IOL 26 may be polished, cleaned, sterilized and packaged by a conventional method known to those skilled in the art.

The subject IOL 26 is used in eye 10 by creating an incision in cornea 12, inserting IOL 26 in anterior chamber 6 preferably using an inserter if desired, opening smooth, serrated or toothed fissure edges 58 of tissue clasp 38 with a surgical instrument, allowing smooth, serrated or toothed fissure edges 58 to close and pinch and/or pierce relatively non-mobile peripheral edge 40 and closing the incision in accordance with methods known to those skilled in the art.

IOL 26 of the present invention provides for a refractive lens suitable for use in anterior chamber 6 of eye 10. IOL 26 has haptic elements 32 with functional characteristics that minimize or eliminate axial displacement along optical axis OA—OA of eye 10 and lens contact in the angle 7 of anterior chamber 6 thereby preventing damage to delicate eye tissues such as the trabecular meshwork 17 and the corneal endothelium 4. IOL 26 designed as described herein is also advantageous because one or a few lens sizes suitably fit eyes 10 of most sizes since the position of attachment to iris 14 may be varied slightly. By providing a "universal" lens such as that of the present invention, clinical risks to patients due to improperly sized lenses in angle 7 are minimized. Likewise, manufacturers' need to produce IOLs of many sizes to fit eyes of many sizes is eliminated, thus reducing production and inventory costs associated therewith. Ophthalmologists also benefit from subject IOL 26 in that time is saved by eliminating the need to determine each patient's particular eye size and costs associated with maintaining large inventories of varying sized lenses.

While there is shown and described herein certain specific embodiments of the present invention, it will be manifest to those skilled in the art that various modifications may be made without departing from the spirit and scope of the underlying inventive concept and that the same is not limited to the particular forms herein shown and described except insofar as indicated by the scope of the appended claims.

We claim:

1. An anterior chamber iris fixated intraocular lens to be implanted within an eye generally perpendicular to the eye's optical axis through a small incision comprising:

an outer peripheral edge defining an optic portion;

two or more haptic elements permanently connected to the outer peripheral edge;

an attachment aperture formed through each of said haptic elements, each said attachment aperture defined by an aperture edge;

a channel void formed in each of said aperture edges and extending a defined distance from said aperture edge toward said optic portion;

a tissue clasp formed to extend from a free edge of each said haptic element through to said aperture edge thereof;

wherein each of said haptic elements may be compressed and thereby close said channel void and thus opening said tissue clasps such that said lens may be attached within an eye by releasing said haptic elements and thereby allowing said tissue clasp to close with iris tissue therein.

2. The intraocular lens of claim 1 wherein a portion of said haptic elements and the optic portion are formed of a foldable or compressible material.

3. The intraocular lens of claim 1 wherein at least a portion of said haptic elements and the optic portion are formed from differing materials.

4. The intraocular lens of claim 1 wherein said tissue clasps and said optic portion are formed from differing materials.

5. The intraocular lens of claim 1 wherein said tissue clasps are made from a material relatively more rigid than that of said optic portion.

6. The intraocular lens of claim 1 wherein said intraocular lens is formed from one or more materials selected from the group consisting of silicone polymers, hydrocarbon and fluorocarbon polymers, hydrogels, soft acrylic polymers, polyester, polyamides, polyurethane, silicone polymers with hydrophilic monomer units, fluorine-containing polysiloxane elastomers and combinations thereof.

7. The intraocular lens of claim 1 wherein said lens optic portion and haptics are formed from a hydrogel material and said tissue clasps are formed from polymethylmethacrylate.

8. The intraocular lens of claim 1 wherein said lens optic portion is formed from an acrylic material.

9. The intraocular lens of claim 1 wherein said lens optic portion is formed from a silicone material.

10. The intraocular lens of claim 1 wherein a glare reduction zone is formed adjacent to the outer peripheral edge of the optic portion.

11. The intraocular lens of claim 1 wherein said tissue clasps are manufactured from a relatively rigid hydrogel, polymethylmethacrylate or polyamide material.

12. The intraocular lens of claim 1 wherein said lens has two haptic elements.

13. The intraocular lens of claim 1 wherein said tissue clasp has smooth, serrated or toothed edges.

14. The intraocular lens of claim 1 wherein said haptic elements may be compressed to open said tissue clasp.

15. A method of manufacturing the intraocular lens of claim 1 comprising:

forming a disk from one or more suitable materials, machining said lens from said disk.

16. A method of manufacturing the intraocular lens of claim 1 comprising:

molding said lens from one or more suitable materials in removable molds, and removing said lens from said molds.

17. A method of using the intraocular lens of claim 1 comprising:

creating an incision in a cornea of an eye, inserting said intraocular lens in an anterior chamber of said eye, and securing said intraocular lens within the anterior chamber.

18. A method of using the intraocular lens of claim 1 comprising:

creating an incision in a cornea of an eye, inserting said intraocular lens in an anterior chamber of said eye using an inserter, and securing said intraocular lens within the anterior chamber using tissue clasps.

* * * * *